United States Patent
Yamada et al.

(10) Patent No.: US 11,964,125 B2
(45) Date of Patent: Apr. 23, 2024

(54) DRUG SOLUTION INJECTION SYSTEM, DRUG SOLUTION INJECTION DEVICE, DRUG SOLUTION INJECTION METHOD, AND PROGRAM

(71) Applicant: DAIKEN MEDICAL CO., LTD., Osaka (JP)

(72) Inventors: Keiichi Yamada, Osaka (JP); Ryo Takuwa, Osaka (JP)

(73) Assignee: DAIKEN MEDICAL CO., LTD., Osaka (JP)

( * ) Notice: Subject to any disclaimer, the term of this patent is extended or adjusted under 35 U.S.C. 154(b) by 884 days.

(21) Appl. No.: 17/040,116

(22) PCT Filed: Mar. 26, 2019

(86) PCT No.: PCT/JP2019/012844
§ 371 (c)(1),
(2) Date: Sep. 22, 2020

(87) PCT Pub. No.: WO2019/189175
PCT Pub. Date: Oct. 3, 2019

(65) Prior Publication Data
US 2021/0023294 A1    Jan. 28, 2021

(30) Foreign Application Priority Data
Mar. 27, 2018    (JP) ................. 2018-059567

(51) Int. Cl.
*A61M 5/142* (2006.01)
*G16H 20/17* (2018.01)

(52) U.S. Cl.
CPC ............ *A61M 5/142* (2013.01); *G16H 20/17* (2018.01); *A61M 2005/14208* (2013.01); *A61M 2205/583* (2013.01); *A61M 2205/6018* (2013.01)

(58) Field of Classification Search
CPC ........ A61M 5/142; A61M 2005/14208; A61M 2205/583; A61M 2205/6018;
(Continued)

(56) References Cited

U.S. PATENT DOCUMENTS

| 6,790,198 B1 | 9/2004 | White et al. |
| 2003/0140928 A1 | 7/2003 | Bui et al. |

(Continued)

FOREIGN PATENT DOCUMENTS

| EP | 2 273 402 | 1/2011 |
| EP | 2 273 403 | 1/2011 |

(Continued)

OTHER PUBLICATIONS

International Search Report dated Jun. 25, 2019 in International (PCT) Application No. PCT/JP2019/012844.

(Continued)

*Primary Examiner* — Theodore J Stigell
(74) *Attorney, Agent, or Firm* — Wenderoth, Lind & Ponack, L.L.P.

(57) ABSTRACT

A medical fluid injection device includes a pump, a communication part, a pump control part, and a storage part. The pump control part is configured to control the pump to start a medical fluid injection when the communication part receives a start signal, and stop the medical fluid injection when the communication part receives a stop signal. The storage part is configured to store start inputter information together with start instruction information indicating that an instruction to start the medical fluid injection is given, and stop inputter information together with stop instruction information indicating that an instruction to stop the medical fluid injection is given.

5 Claims, 8 Drawing Sheets

(58) Field of Classification Search
CPC .. A61M 2005/1405; A61M 2205/3561; A61M 2205/52; G16H 20/17; G16H 40/63
See application file for complete search history.

(56) References Cited

U.S. PATENT DOCUMENTS

| | | |
|---|---|---|
| 2003/0204274 A1 | 10/2003 | Ullestad et al. |
| 2004/0176984 A1* | 9/2004 | White ................... G16H 20/17 128/904 |
| 2005/0144043 A1 | 6/2005 | Holland et al. |
| 2005/0240441 A1 | 10/2005 | Suzuki et al. |
| 2005/0278194 A1 | 12/2005 | Holland et al. |
| 2006/0089854 A1 | 4/2006 | Holland et al. |
| 2006/0089855 A1 | 4/2006 | Holland et al. |
| 2006/0100907 A1 | 5/2006 | Holland et al. |
| 2006/0116639 A1 | 6/2006 | Russell |
| 2006/0265186 A1 | 11/2006 | Holland et al. |
| 2007/0213598 A1 | 9/2007 | Howard et al. |
| 2007/0214003 A1 | 9/2007 | Holland et al. |
| 2007/0251835 A1 | 11/2007 | Mehta et al. |
| 2007/0253021 A1 | 11/2007 | Mehta et al. |
| 2007/0255116 A1 | 11/2007 | Mehta et al. |
| 2008/0133265 A1 | 6/2008 | Silkaitis et al. |
| 2009/0270810 A1 | 10/2009 | DeBelser et al. |
| 2013/0191513 A1 | 7/2013 | Kamen et al. |
| 2013/0297330 A1 | 11/2013 | Kamen et al. |
| 2013/0317837 A1 | 11/2013 | Ballantyne et al. |
| 2016/0147978 A1* | 5/2016 | Adams ................... G16H 10/60 705/2 |

FOREIGN PATENT DOCUMENTS

| | | |
|---|---|---|
| JP | 2000-042102 | 2/2000 |
| JP | 2003-180826 | 7/2003 |
| JP | 2005-523793 | 8/2005 |
| JP | 2008-521500 | 6/2008 |
| JP | 2010-524050 | 7/2010 |
| JP | 2013-192890 | 9/2013 |
| JP | 2016-509284 | 3/2016 |
| WO | 2009/124133 | 10/2009 |

OTHER PUBLICATIONS

Extended European Search Report dated Apr. 20, 2021 in European Patent Application No. 19777169.4.
Office Action dated Feb. 28, 2022 in corresponding Chinese Application No. 201980020072.3, with English translation.

* cited by examiner

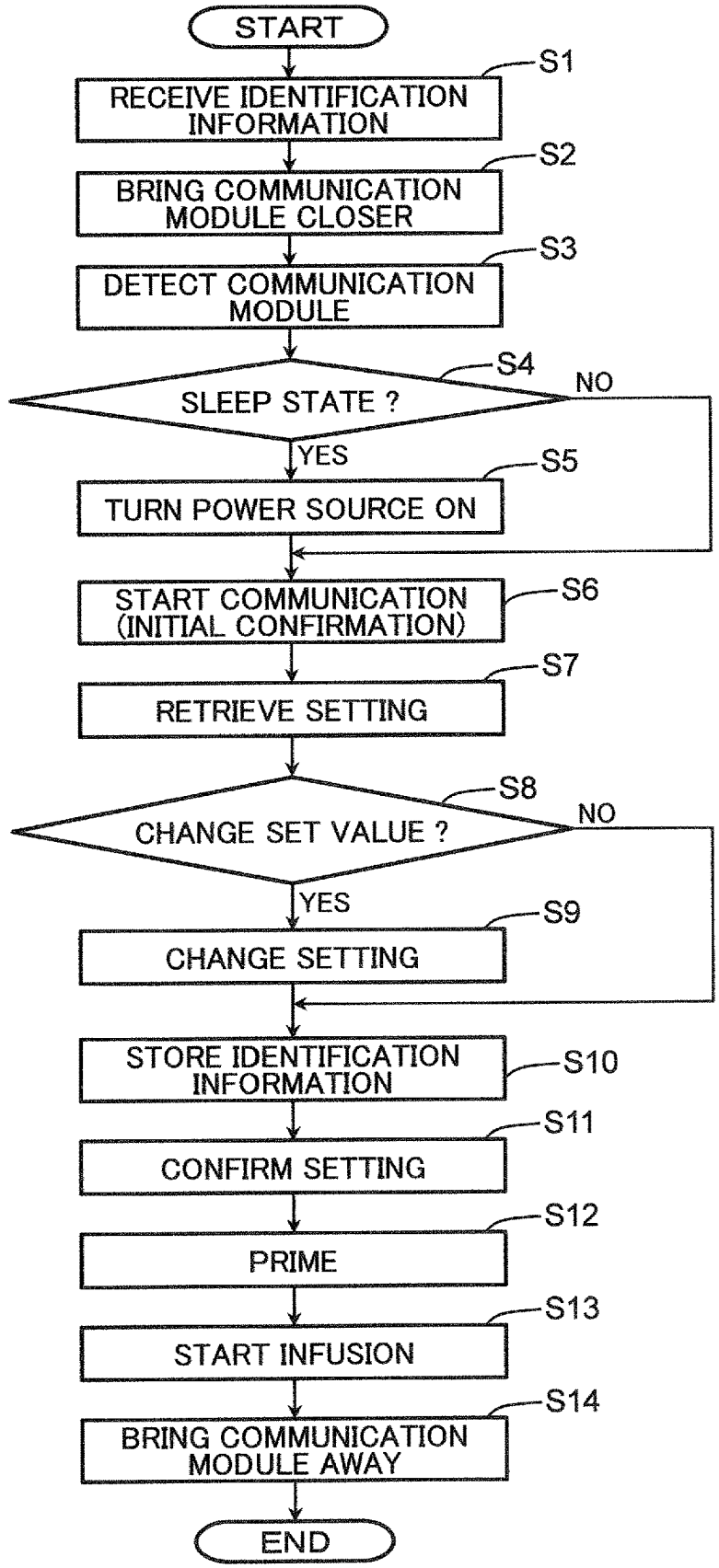

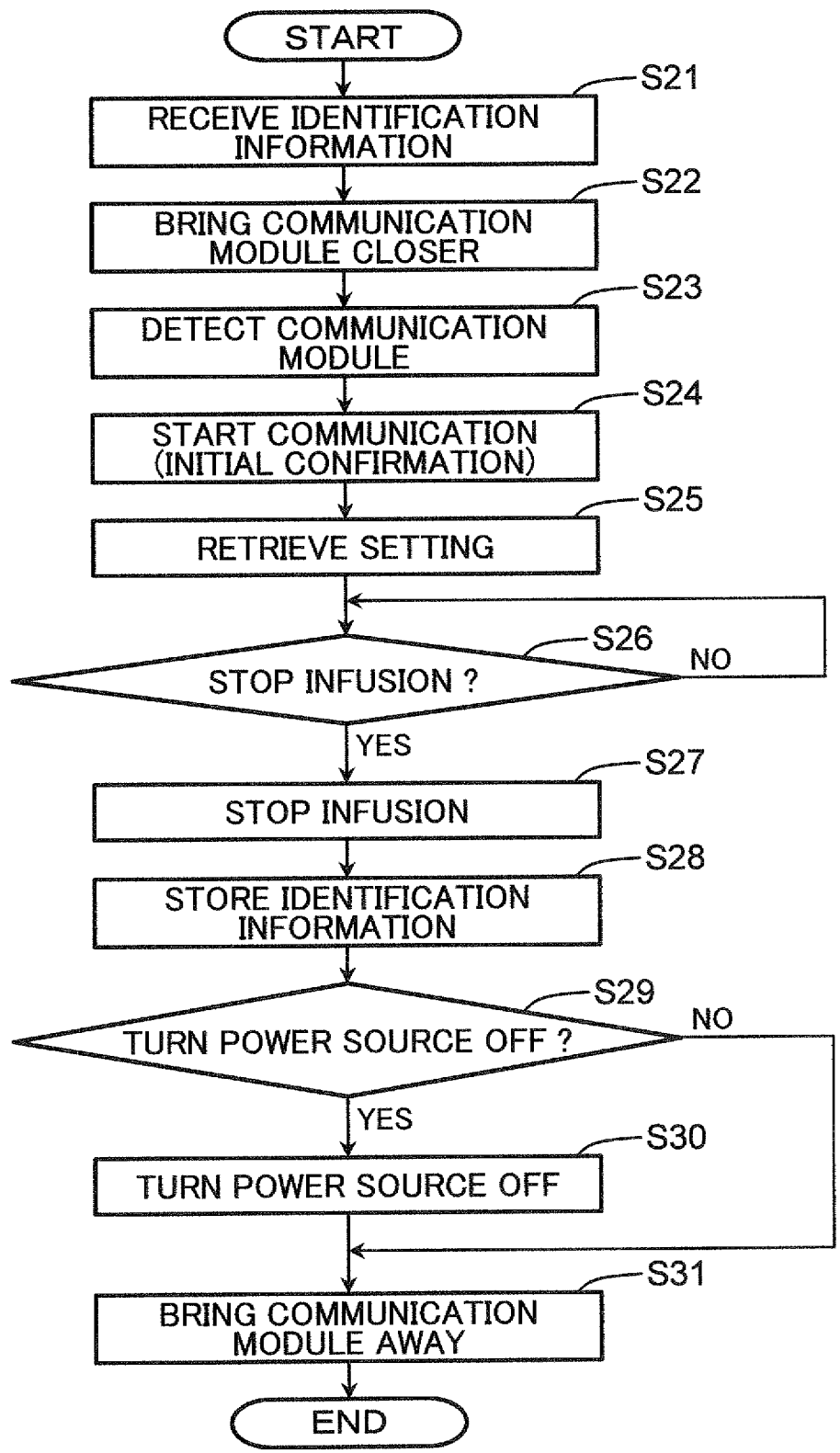

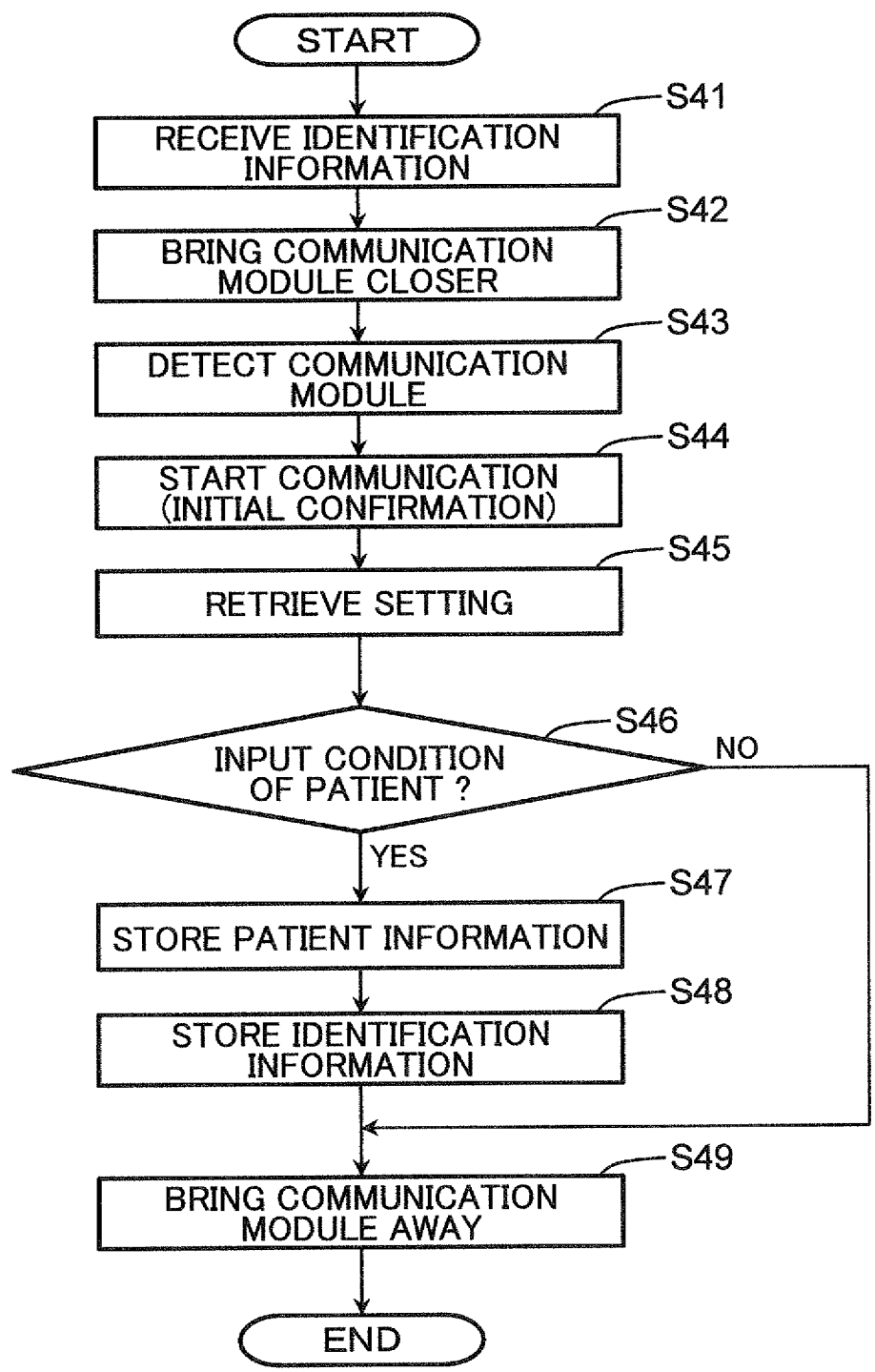

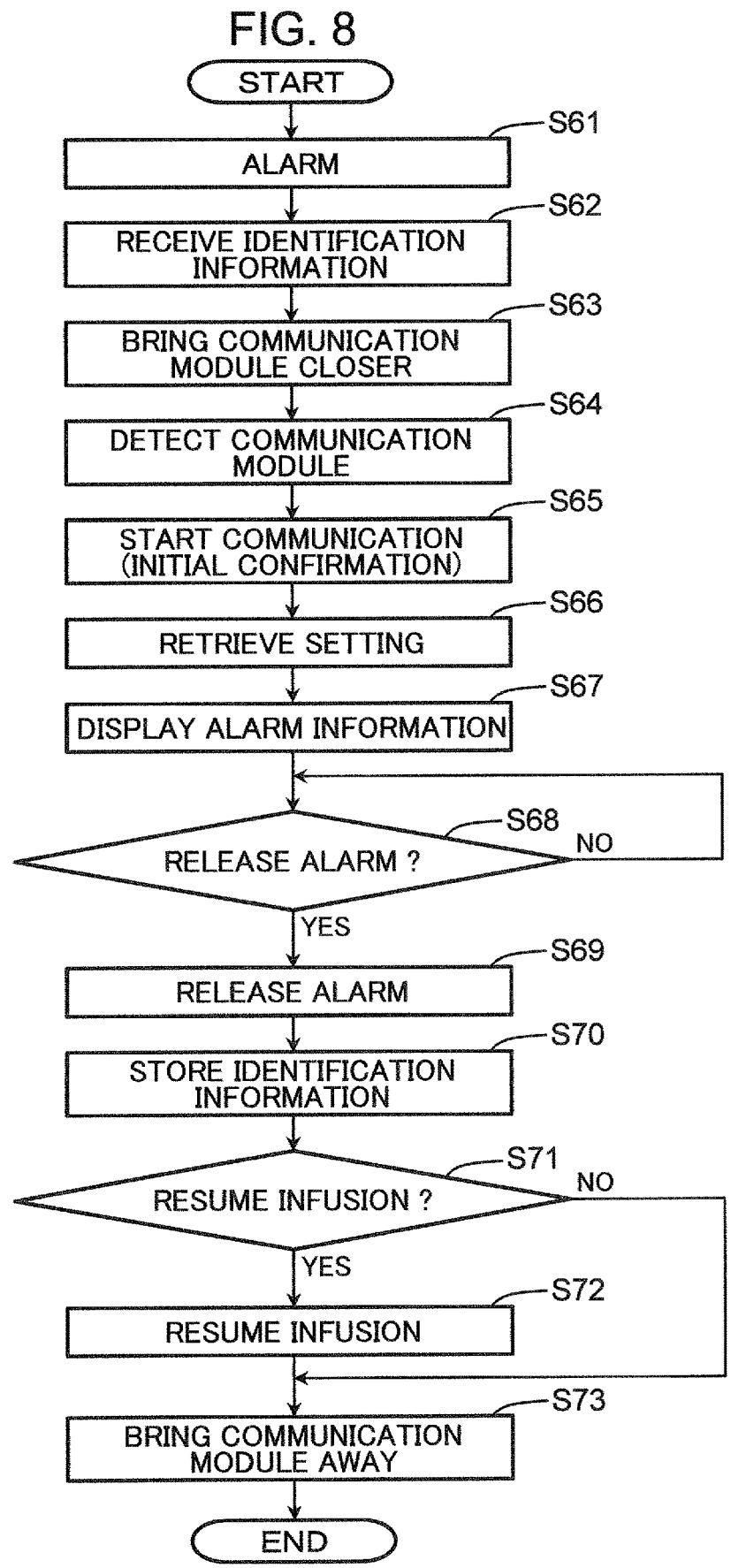

DRUG SOLUTION INJECTION SYSTEM, DRUG SOLUTION INJECTION DEVICE, DRUG SOLUTION INJECTION METHOD, AND PROGRAM

TECHNICAL FIELD

The present invention relates to a medical fluid injection system, a medical fluid injection device, a medical fluid injection method, and a program for injecting medical fluid into a patient.

BACKGROUND ART

Conventionally, medical fluid injection devices for injecting medical fluid contained in a container into the body of a patient have been known.

For example, Japanese Unexamined Patent Publication No. 2000-042102 (hereinafter, "JP 2000-042102") discloses a medical fluid injection system that is provided with: a medical fluid injection device including slave control means having a temporary storage part for storing an administration schedule and a consumption history of medical fluid; and an external control device including main control means having a programming part for controlling a manipulation part and a display part, the main control means executing transmission and reception of the administration schedule and the consumption history with the temporary storage part, the main control means executing the transmission and the reception based on a specified identification signal with connection with the slave control means, and connecting means for connecting the medical fluid injection device.

In this medical fluid injection system disclosed in JP 2000-042102, when an operation switch provided in a flow rate control unit of the medical fluid injection device is turned on, medical fluid injection is started according to operation information having been inputted in the medical fluid injection device.

By the way, in the healthcare field, a patient is generally nursed by a plurality of nurses working in shifts. Then, sometimes arises the need to confirm at a later date who, among a plurality of healthcare practitioners such as doctors and nurses, is engaged in a treatment of medical fluid injection to a certain patient.

However, the medical fluid injection system disclosed in JP 2000-042102 shows no consideration for confirming at a later date who, among a plurality of healthcare practitioners, turns on an operation switch provided in a flow rate control unit of the medical fluid injection device. Thus, a burdensome work of creating, separately from the medical fluid injection system, a nursing record is required to confirm at a later date the healthcare practitioner who is engaged in the treatment of medical fluid injection to the patient.

SUMMARY OF INVENTION

An object of the present invention is to provide a medical fluid injection system, a medical fluid injection device, a medical fluid injection method, and a program that make it possible to confirm who, among a plurality of healthcare practitioners, is engaged in a treatment of medical fluid injection to a patient.

A medical fluid injection system according to the present invention is adapted for injecting medical fluid into a patient. The medical fluid injection system includes: a plurality of medical fluid injection devices respectively corresponding to the plurality of patients; and at least one external device provided outside the plurality of medical fluid injection devices, the at least one external device being for giving an instruction of starting medical fluid injection and an instruction of stopping the medical fluid injection to the plurality of medical fluid injection devices.

Each of the medical fluid injection devices includes a pump for supplying the medical fluid, a communication part, a pump control part, and a storage part. The communication part is configured to receive: a start signal outputted from the external device to instruct a start of the medical fluid injection; a signal outputted from the external device, the signal carrying start inputter information for identifying a start inputter who executes an input to the external device to instruct the start of the medical fluid injection; a stop signal outputted from the external device to instruct a stop of the medical fluid injection; and a signal outputted from the external device, the signal carrying stop inputter information for identifying a stop inputter who executes an input to the external device to instruct the stop of the medical fluid injection. The pump control part is configured to control the pump to start the medical fluid injection when the communication part receives the start signal, and to stop the medical fluid injection when the communication part receives the stop signal. The storage part is configured to store the start inputter information together with start instruction information including information indicating that the instruction of starting the medical fluid injection is given, and the stop inputter information together with stop instruction information including information indicating that the instruction of stopping the medical fluid injection is given.

According to the present invention, it is possible to confirm who, among a plurality of healthcare practitioners, is engaged in a treatment of medical fluid injection to a patient.

BRIEF DESCRIPTION OF DRAWINGS

FIG. 5 is a flowchart showing a medical fluid injection method in the embodiment of the present invention, and showing an operation routine of starting medical fluid injection.

FIG. 6 is a flowchart showing the medical fluid injection method in the embodiment, and showing an operation routine of stopping medical fluid injection.

FIG. 7 is a flowchart showing the medical fluid injection method in the embodiment, and showing an operation routine of confirming a condition of a patient.

FIG. 8 is a flowchart showing the medical fluid injection method in the embodiment, and shows an operation routine of stopping an alarm.

DESCRIPTION OF EMBODIMENTS

Hereinafter, embodiments of the present invention will be described with reference to the drawings. It should be noted that the below-described embodiments are specific examples of the present invention, and are not intended to limit the claimed scope of the present invention.

[Medical Fluid Injection System]

Figure 1:
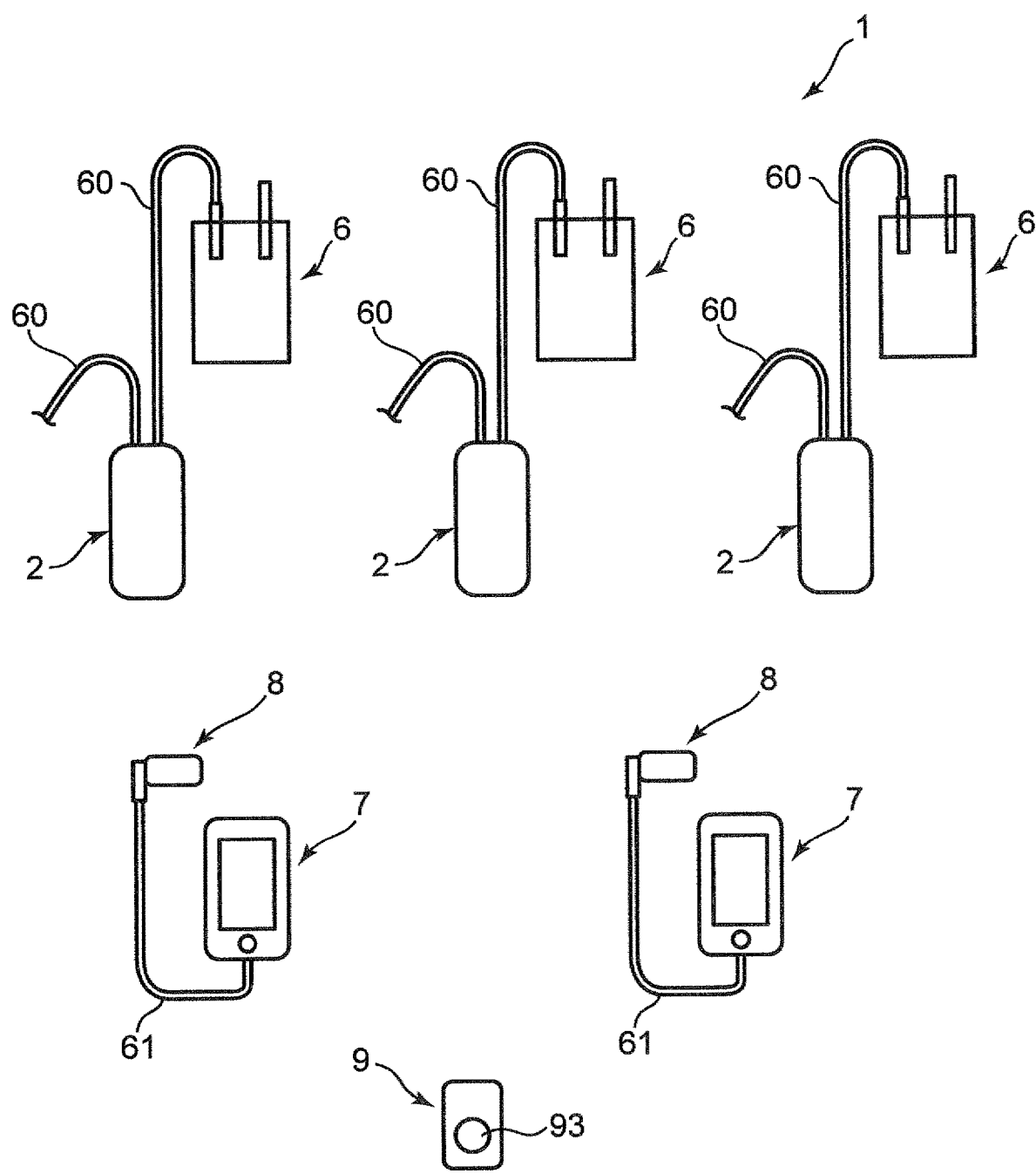
FIG. 1 is a plan view of a medical fluid injection system according to an embodiment of the present invention.
Figure 2:
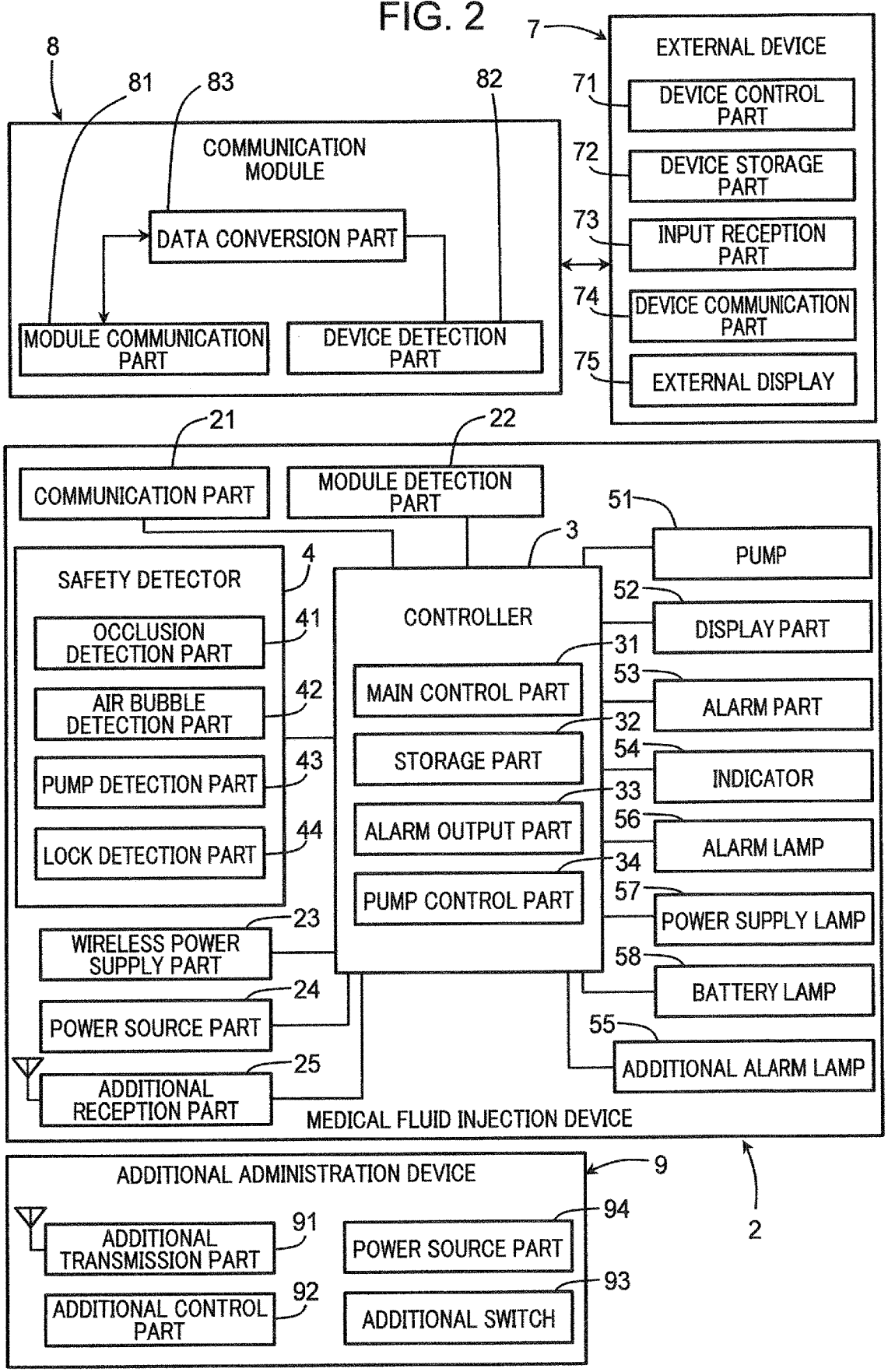
FIG. 2 is a block diagram showing a functional configuration of the medical fluid injection system according to the embodiment.
Figure 3:
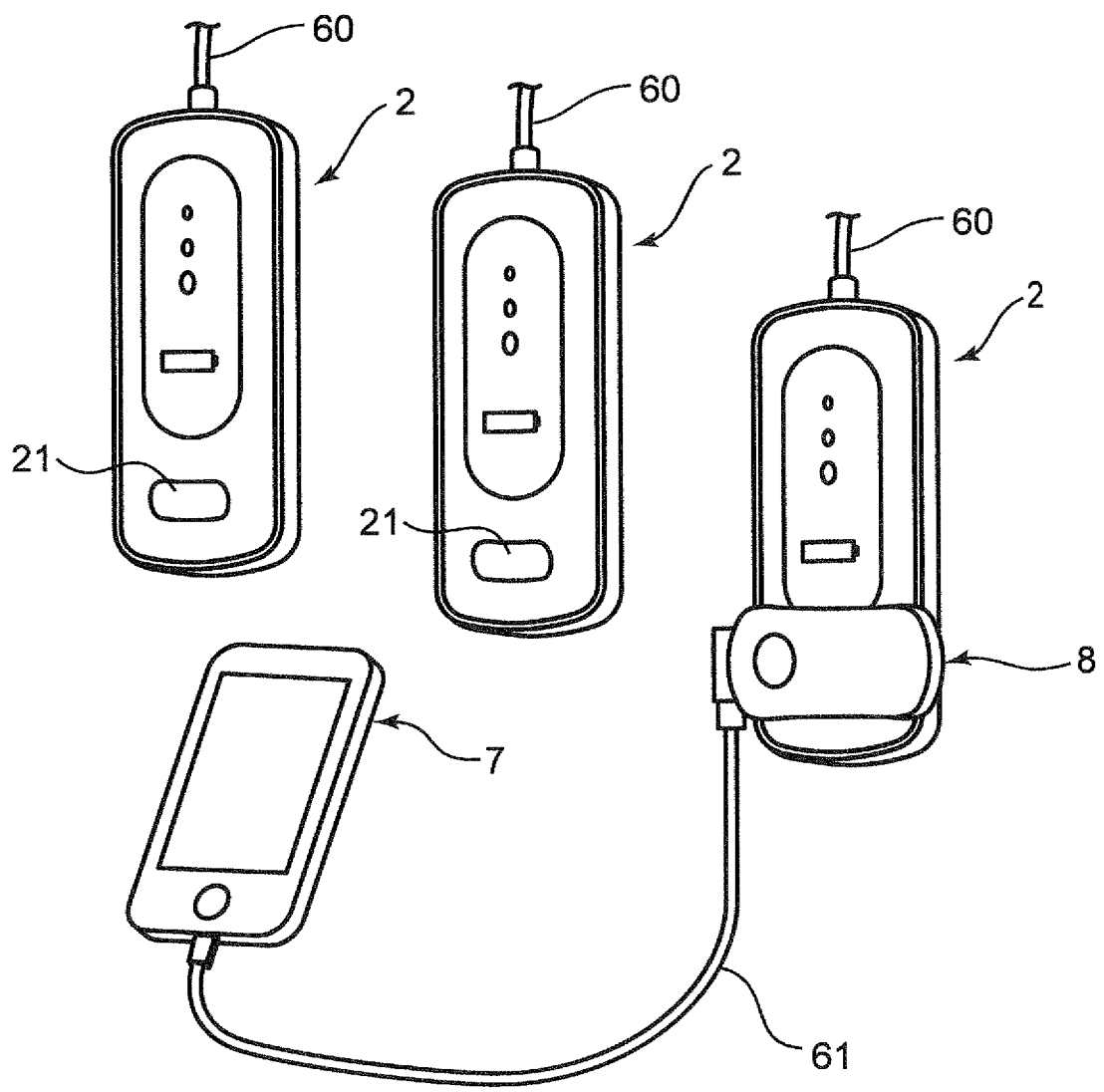
FIG. 3 is a perspective view showing a state in which an external device, a communication module, and a specified medical fluid injection device are connected to each other in the medical fluid injection system according to the embodiment.
Figure 4:
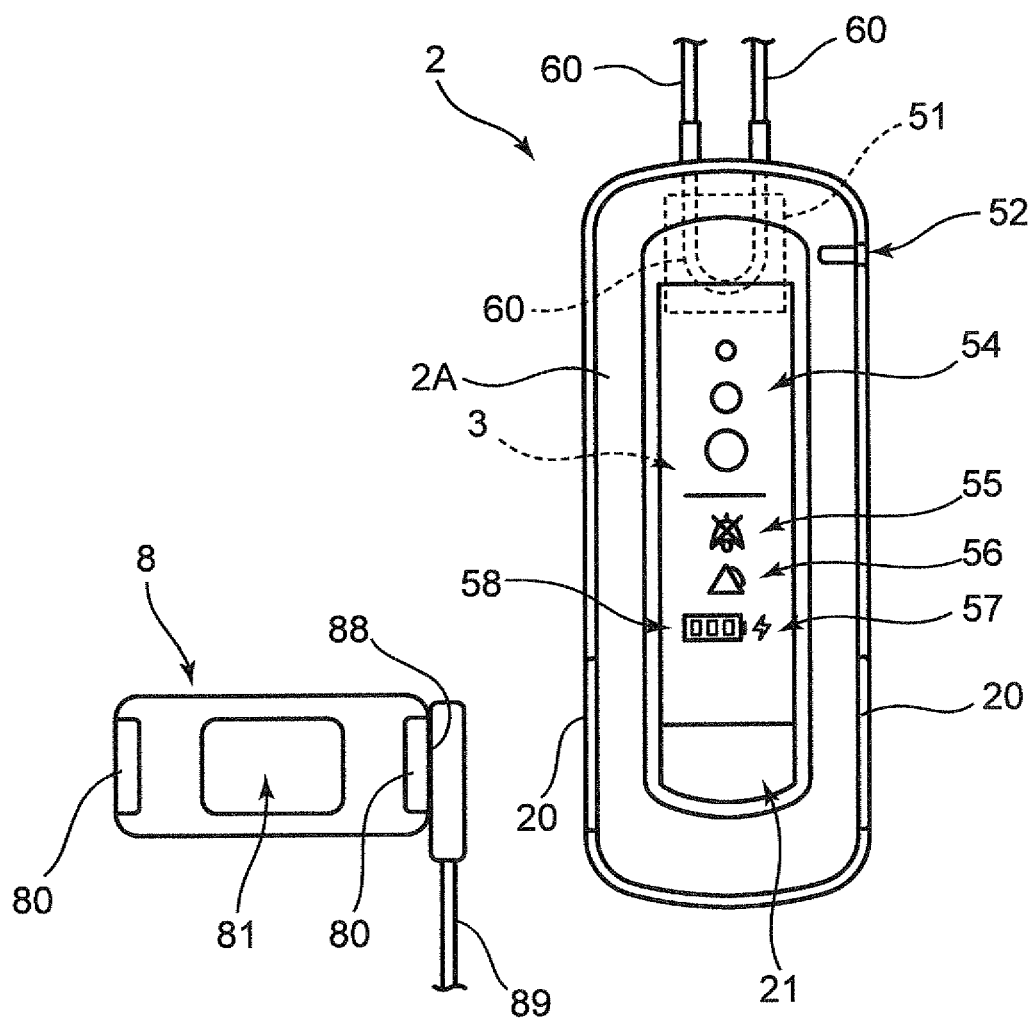
FIG. 4 is a plan view showing a medical fluid injection device and a communication module according to the embodiment of the present invention.

FIG. 1 is a plan view of a medical fluid injection system 1 according to an embodiment of the present invention. FIG. 2 is a block diagram showing a functional configuration of the medical fluid injection system 1 according to the embodiment. FIG. 3 is a perspective view showing a state in which an external device 7, a communication module 8, and a specified medical fluid injection device 2 are connected to each other in the medical fluid injection system 1 according to the embodiment. FIG. 4 is a plan view showing a medical fluid injection device 2 and a communication module 8 according to the embodiment.

The medical fluid injection system 1 is adapted for respectively injecting into a plurality of patients medical fluid adequate to a symptom and the like of each patient at a set value set in advance for each patient. The medical fluid injection system 1 can be used to inject various medical fluids, such as anticoagulants, inotropes, anesthetics, carcinostatics, and antibiotics, into a patient. However, the medical fluids to be used in the medical fluid injection system 1 are not limited to these fluids.

As shown in FIG. 1, the medical fluid injection system 1 includes a plurality of medical fluid injection devices 2, a plurality of external devices 7, a plurality of communication modules 8, a plurality of medical fluid containers 6, a plurality of medical fluid tubes 60, and an additional administration device 9.

Each medical fluid container 6 contains medical fluid adequate to a symptom of a certain patient. The medical fluid container 6 is connected with the medical fluid tube 60. The medical fluid within the medical fluid container 6 is supplied through the medical fluid tube 60 by means of a later described pump 51 provided in the medical fluid injection device 2, and is injected into a patient.

Each external device 7 has, for the medical fluid injection device 2, a function of instructing a start of medical fluid injection, a function of instructing a stop of medical fluid injection, a function of setting a set value for medical fluid injection, a function of changing the set value for medical fluid injection, a function of storing a history of medical fluid injections, and a function of displaying the history of medical fluid injections. Besides, each external device 7 has a function of receiving an instruction input by a healthcare practitioner to start or stop medical fluid injection, an instruction input by a healthcare practitioner to set or change a set value for medical fluid injection.

Each external device 7 is provided outside medical fluid injection devices 2, and is configured to be separable from the medical fluid injection devices 2. In the present embodiment, each external device 7 is configured to be used by a plurality of healthcare practitioners such as doctors and nurses. However, a certain external device 7 may be assigned in advance to a specified healthcare practitioner. In the specific example shown in FIG. 1, the plurality of external devices 7 include a first external device 7 and a second external device 7. However, the number of external devices 7 may be three or more, or may be one.

Each communication module 8 is interposed between the external device 7 and the medical fluid injection device 2. Each communication module 8 has a function of selectively allowing transmission and reception of information between the external device 7 and a specified medical fluid injection device 2, a function of receiving a signal outputted from the external device 7 and outputting the signal to the medical fluid injection device 2, and a function of receiving a signal outputted from the medical fluid injection device 2, and outputting the signal to the external device 7.

Each communication module 8 is provided outside the medical fluid injection devices 2, and is configured to be separable from the medical fluid injection devices 2. In the present embodiment, each communication module 8 is assigned in advance to the corresponding external device 7. An external device 7 and the corresponding communication module 8 are configured to be connected to each other via a cable 61 to execute wire communication with each other. However, the external device 7 and the corresponding communication module 8 may be configured to execute wireless-communication with each other. In the specific example shown in FIG. 1, the plurality of communication modules 8 includes a first communication module 8 and a second communication module 8. However, the number of the communication modules 8 may be three or more, or may be one.

Each medical fluid injection device 2 has a function of starting medical fluid injection in accordance with an instruction by a signal outputted from the external device 7, a function of supplying the medical fluid in order to inject medical fluid into a patient in accordance with a set value set by a signal outputted from the external device 7, a function of stopping medical fluid injection in accordance with an instruction by a signal outputted from the external device 7, a function of storing a history of medical fluid injections, and a function of transmitting information regarding the history to the external device 7 via the communication module 8.

In the specific example shown in FIG. 1, the plurality of medical fluid injection devices 2 includes a first medical fluid injection device 2, a second medical fluid injection device 2, and a third medical fluid injection device 2. However, the number of medical fluid injection devices 2 may be four or more. These medical fluid injection devices 2 have the same configuration.

The plurality of medical fluid injection devices 2 are respectively assigned to the plurality of patients in advance. In other words, each patient uses an exclusive medical fluid injection device 2. Specifically, for example, a patient A uses the first medical fluid injection device 2, a patient B uses the second medical fluid injection device 2, and a patient C uses the third medical fluid injection device 2. Accordingly, when a medical fluid injection device 2 is specified, a certain patient is specified.

The additional administration device 9 is adapted for outputting, to a later described controller 3, an instruction of increasing the dose of medical fluid to be sent out. For example, in the case that medical fluid is anesthetic, a patient is allowed to manipulate the additional administration device 9 to increase the administration dose of the anesthetic depending on an increase in the pain to thereby alleviate the pain. Namely, the additional administration device 9 which is provided outside the medical fluid injection device 2 to give an instruction regarding medical fluid injection to the medical fluid injection device 2 is an external device for sending an additional instruction.

An overall configuration of the medical fluid injection system 1 is as described above. Hereinafter, each device constituting the medical fluid injection system 1 will be further specifically described.

[Medical Fluid Injection Device]

As shown in FIGS. 2 and 4, each medical fluid injection device 2 includes a pump 51, a communication part 21, a module detection part 22, a controller 3, a safety detector 4, and a housing 2A accommodating those.

The pump 51 has a function of supplying medical fluid to a patient from the medical fluid container 6 via the medical fluid tube 60. The pump 51 is not limited to have a particular mechanism but it is sufficient that the pump 51 has any mechanism which can supply the medical fluid to a patient. The pump 51 may be one, for example, which can supply the medical fluid in the medical fluid tube 60 to a patient at a constant flow rate by pressing a part of the medical fluid tube 60 so that the medical fluid tube 60 peristaltically moves at a predetermined cycle. The pump 51 is accommodated in an unillustrated chamber part provided in a housing 2A, and is detachably provided on the housing 2A.

The communication part 21 has a function of receiving various signals outputted from the external device 7. The signals outputted from the external device 7 include, for instance, a start signal for instructing a start of medical fluid injection, a signal carrying start inputter information for identifying a start inputter who executes an input to the external device 7 to instruct the start of the medical fluid injection, a stop signal for instructing a stop of the medical fluid injection, a signal carrying stop inputter information for identifying a stop inputter who executes an input to the external device 7 to instruct the stop of the medical fluid injection, a set value signal for instructing setting or changing of a set value for medical fluid injection, and a signal carrying setting inputter information for identifying a setting inputter who executes an input to the external device 7 to instruct setting or changing of the set value for the medical fluid injection. However, the signals are not limited to these signals.

In the present embodiment, the communication module 8 is interposed between the medical fluid injection device 2 and the external device 7. Therefore, the communication part 21 receives a signal outputted from the external device 7 via the communication module 8, and outputs to the communication module 8 a signal to be transmitted to the external device 7. In the present embodiment, the communication part 21 transmits and receives information by a way of a later described module communication part 81 of the communication module 8. The module detection part 22 has a function of detecting, in cooperation with a later described device detection part 82 provided in the communication module 8, that the communication module 8 can communicate with the medical fluid injection device 2.

The controller 3 is provided with a computer including a CPU (Central Processing Unit), a ROM (Read Only Memory) that stores various control programs, a RAM (Random Access Memory) that is used as a working area for the CPU.

As shown in FIG. 2, the controller 3 includes a main control part 31, a storage part 32, an alarm output part 33, and a pump control part 34. In the controller 3, the main control part 31, the storage part 32, the alarm output part 33, and the pump control part 34 accomplish their functions owing to the CPU executing the control programs.

The main control part 31 is adapted for controlling an overall operation of the medical fluid injection device 2.

The storage part 32 stores the start inputter information together with start instruction information including information indicating that an instruction of starting medical fluid injection is given. Besides, the storage part 32 stores the stop inputter information together with stop instruction information including information indicating that an instruction of stopping medical fluid injection is given. Further, the storage part 32 stores the setting inputter information together with setting instruction information including information indicating that an instruction of setting or changing the set value for medical fluid injection is given.

It should be noted that the start instruction information stored in the storage part 32 includes not only the start instruction information carried by the start signal outputted from the external device 7 but also the start instruction information carried by a start signal (signal of starting injection of increased dose) outputted from the additional administration device 9 serving as an external device for sending an additional instruction. Further, the start inputter information stored in the storage part 32 includes not only the start inputter information carried by the start signal outputted from the external device 7, but also the start inputter information carried by the start signal (signal of starting injection of increased dose) outputted from the additional administration device 9. In the present embodiment, the start inputter information for injection of increased dose is set in advance for a patient who is supposed to manipulate the additional administration device 9.

Similarly, the stop instruction information stored in the storage part 32 includes not only the stop instruction information carried by the stop signal outputted from the external device 7 but also the stop instruction information carried by a stop signal (signal of stopping injection of increased dose) outputted from the additional administration device 9 serving as an external device for sending an additional instruction. Further, the stop inputter information stored in the storage part 32 includes not only the stop inputter information carried by the stop signal outputted from the external device 7, but also the stop inputter information carried by the stop signal (signal of stopping injection of increased dose) outputted from the additional administration device 9. In the present embodiment, the stop inputter information for injection of increased dose is set in advance for a patient who is supposed to manipulate the additional administration device 9.

The pump control part 34 is configured to control the pump 51 to start the medical fluid injection when the communication part 21 receives the start signal, and to stop the medical fluid injection when the communication part 21 receives the stop signal.

The alarm output part 33 has a function of notifying, in response to an abnormality state of the medical fluid injection device 2 detected by a safety detector 4, a healthcare practitioner of the abnormality by means of an alarm lamp 56.

As shown in FIG. 2, the safety detector 4 includes an occlusion detection part 41, an air bubble detection part 42, a pump detection part 43, and a lock detection part 44.

The occlusion detection part 41 includes a sensor for detecting a presence or an absence of occlusion in a medical fluid tube 60. The occlusion detection part 41 includes, for instance, a pressure sensor for detecting a rise in the pressure in the medical fluid tube 60 due to a cause that the inside space of the medical fluid tube 60 is blocked by a foreign substance, or the medical fluid tube 60 is bent to close up the medical fluid flow.

The air bubble detection part 42 includes a sensor for detecting an air bubble contained in the medical fluid tube 60. The air bubble detection part 42 includes, for instance, an ultrasonic sensor.

The pump detection part 43 includes a sensor for detecting whether the pump 51 is accommodated in the chamber part of the housing 2A or not.

The lock detection part 44 includes a sensor for detecting an open and close state of an unillustrated door which opens and closes the chamber part of the housing 2A.

As shown in FIG. 2 and FIG. 4, each medical fluid injection device 2 further includes a display part 52, an alarm part 53, an indicator 54, an additional alarm lamp 55, an alarm lamp 56, a power supply lamp 57, and a battery lamp 58.

The display part 52 is adapted for displaying an operation state of the medical fluid injection device 2. In the present embodiment, the display part 52 includes a pilot lamp. However, the display part 52 is not limited to the pilot lamp. For instance, the display part 52 may include a liquid crystal display.

The following examples are operation states of the medical fluid injection device 2 that the display part 52 displays. The display part 52 displays, for instance, that a state where the medical fluid injection device 2 and the communication module 8 are able to communicate with each other is established when the communication module 8 is connected with the medical fluid injection device 2. Further, the display part 52 displays that the medical fluid injection device 2 is in the operation of medical fluid injection. Further, the display part 52 displays abnormality states detected by sensors of the occlusion detection part 41, the air bubble detection part 42, the pump detection part 43, and the lock detection part 44. Besides, the display part 52 displays that the medical fluid injection device 2 is in a later described lockout time. Additionally, the display part 52 displays that the medical fluid injection device 2 is suspended.

These operation states are displayed by causing a pilot lamp to emit light in different colors, intermittently, or no light, the pilot lamp serving as the display part 52. Further, in the case that the display part 52 includes a liquid crystal display, the operation states may be displayed by characters, figures, and the like.

The indicator 54 performs a display of notifying the healthcare practitioner of an approximate flow rate of medical fluid injection during medical fluid injection. The indicator 54 has a scrolling portion moving at a velocity depending in accordance with a flow rate.

The additional alarm lamp 55 emits light during suspension of an additional alarm. There is a case that even when a healthcare practitioner catches an alarm sound produced upon a trouble occurring in the medical fluid injection device 2, and turns the alarm sound off (i.e., releases the alarm) after establishing a communication between the medical fluid injection device 2 and the external device 7, the trouble in the medical fluid injection device 2 has not yet been solved. For this case, the medical fluid injection device 2 is configured to produce an additional alarm sound if the trouble in the medical fluid injection device 2 has not yet been solved after the elapse of a given time since the release of the alarm. The additional alarm lamp 55 is put in work in the case where the alarm is released by the healthcare practitioner (in the mute state) but the trouble in the medical fluid injection device 2 has not yet been solved.

The alarm part 53 and the alarm lamp 56 are adapted for notifying the healthcare practitioner of the abnormality in the medical fluid injection device 2 that is detected by the aforementioned safety detector 4. When an abnormality in the medical fluid injection device 2 is detected by the safety detector 4, the alarm output part 33 controls the alarm part 53 and the alarm lamp 56 so that the alarm part 53 produces an alarm sound, and the alarm lamp 56 emits light constantly or intermittently, and the like to notify the healthcare practitioner of the abnormality.

The power supply lamp 57 performs a display to notify the healthcare practitioner that there is little remaining battery power in a later-described power source part 24. The battery lamp 58 performs a display of a remaining battery power of the power source part 24.

Each medical fluid injection device 2 further includes an additional reception part 25. The additional reception part 25 receives an additional administration signal of medical fluid outputted from the additional administration device 9. The additional administration signal is a signal outputted from the additional administration device 9 serving as an external device for sending an additional instruction, and is a start signal for instructing a start of medical fluid injection of an increased dose (signal for starting injection of increased dose). As shown in FIG. 2, the additional administration device 9 includes an additional transmission part 91, an additional control part 92, an additional administration switch 93, and a power source part 94. The additional administration device 9 is operated by the electricity of the power source part 94, and the operation of the additional administration device 9 is controlled by the additional control part 92. When the additional administration switch 93 is manipulated by a patient, the additional transmission part 91 wirelessly transmits to the additional reception part 25 of the medical fluid injection device 2 the additional administration signal of increasing the dose of the medical fluid. When the additional reception part 25 receives the signal, the pump control part 34 controls the pump 51 to increase the flow rate of the medical fluid injection.

However, when the additional reception part 25 receives the signal from the additional administration device 9, the pump control part 34 determines whether a time set in advance (i.e., a lockout time) is elapsed or not since the previous reception of the signal from the additional administration device 9. When determining that the lockout time is not elapsed, the pump control part 34 judges that the instruction from the additional administration device 9 is invalid. This prevents a patient from being injected with an excessive dose of medical fluid. On the other hand, when determining that the lockout time is elapsed, the pump control part 34 sets a drive voltage to supply the medical fluid at an increased flow rate in response to an instruction from the additional administration device 9. After elapse of a time set in advance, the pump control part 34 returns to the drive voltage to supply the medical fluid at the ordinary flow rate (the set flow rate before the increased dose).

As described above, when the additional reception part 25 receives the signal of starting injection of increased dose, the pump control part 34 controls the pump 51 to start the medical fluid injection of an increased dose. Further, when the additional reception part 25 receives a signal of stopping injection of increased dose, the pump control part 34 may control the pump 51 to stop the medical fluid injection of the increased dose. In this case, the pump control part 34 may control the pump 51 to return to the injection rate of the medical fluid at the usual injection rate before the increased dose. The signal for stopping injection of increased dose is a signal outputted from the additional administration device 9 serving as an external device for sending an additional instruction, and is a stop signal for instructing a stop of medical fluid injection of the increased dose.

Each medical fluid injection device 2 further includes a wireless power supply part 23 and a power source part 24. In the present embodiment, the power source part 24 includes a rechargeable battery. When charging the power source part 24, the medical fluid injection device 2 is, for instance, arranged on an unillustrated wireless charging unit for performing charging in an electromagnetic induction way. In this way, an electric current is generated in a coil in the wireless power supply part 23 through electromagnetic induction to thereby charge the power source part 24.

In the present embodiment, each medical fluid injection device 2 does not include such manipulation units as a switch for starting medical fluid injection, a switch for stopping medical fluid injection, an input unit for inputting a changed set value for medical fluid injection. Besides, in the present embodiment, each medical fluid injection device 2 does not include such display as a liquid crystal display for displaying characters.

Further, in the present embodiment, the transmission and reception of signals between the medical fluid injection device 2 and the communication module 8 is executed via a wireless data communication by use of an infrared communication. Additionally, the charging of the medical fluid injection device 2 is performed in the wireless charging such as an electromagnetic induction way. Accordingly, there is no need to provide an opening for terminal connection that is required in the case of a wire data communication, and an opening for terminal connection that is required in the case of a wired charging. Thus, the medical fluid injection device 2 according to the present embodiment is excellent in drip-proof performance.

[Communication Module]

The communication module 8 is adapted for executing the transmission and reception of information between the medical fluid injection device 2 and the external device 7. As shown in FIG. 2 and FIG. 4, the communication module 8 includes a pair of engaging parts 80 serving as the connecting part, a module communication part 81, a device detection part 82, and a data conversion part 83.

When the medical fluid injection device 2 and the external device 7 execute transmission and reception of information, the communication module 8 is connected at a predetermined location of the medical fluid injection device 2. The medical fluid injection device 2 includes a pair of engaged parts 20 with which the pair of engaging parts 80 is engaged. The pair of engaging parts 80 of the communication module 8 is engaged with the pair of engaged parts 20 of the medical fluid injection device 2 to connect the communication module 8 to the medical fluid injection device 2 as shown in FIG. 3. In this connection state, the module communication part 81 of the communication module 8 is arranged at a position facing the communication part 21 of the medical fluid injection device 2 and neighboring or contacting to the communication part 21. In the present embodiment, the module communication part 81 of the communication module 8 and the communication part 21 of the medical fluid injection device 2 execute transmission and reception of information between them in infrared communication which is a wireless data communication using infrared rays.

The device detection part 82 of the communication module 8 and the module detection part 22 of the medical fluid injection device 2 are adapted for detecting that the communication module 8 can communicate with the medical fluid injection device 2. The detection parts 22, 82 are provided with, for example, an optical sensor or a magnetic sensor. However, the detection parts are not limited to these sensors. The optical sensor is a sensor that detects an intermittence and an intensity of light and converts to an electric signal. The magnetic sensor is a sensor that detects a magnetic flux density of a magnet and converts to an electric signal.

When the detection parts 22, 82 detect that the communication module 8 can communicate with the medical fluid injection device 2, the device detection part 82 outputs an electric signal to a data conversion part 83, and the data conversion part 83 allows the external device 7 and the medical fluid injection device 2 to transmit and receive information between them. Besides, the data conversion part 83 further functions as an adaptor for converting data having a different protocol to communicable data, in addition to the function for executing transmission and reception of information. In the present embodiment, the medical fluid injection device 2 and the communication module 8 are configured to transmit and receive information between them in infrared communication, and the external device 7 and the communication module 8 are configured to transmit and receive information between them according to Universal Serial Bus (USB) protocol. The data conversion part 83 converts data having different protocol to communicable data between the medical fluid injection device 2 and the external device 7.

[External Device]

The external device 7 has various functions described above. As far as the external device 7 has these various functions, it is not limited to the specific configurations. As the external device 7, for instance, a portable information communication terminal such as a smartphone, a tablet terminal, and a laptop computer may be used. In the specific examples shown in FIG. 1 and FIG. 3, a smartphone is used as the external device 7.

The external device 7 includes a device control part 71, a device storage part 72, an input reception part 73, a device communication part 74, and a display 75. The device control part 71 controls the operation of the external device 7. The display 75 includes, for instance, a liquid crystal display.

The input reception part 73 has a function of receiving various inputs by a healthcare practitioner. The input reception part 73 receives, for instance, an input for starting medical fluid injection executed by a start inputter who starts the medical fluid injection, an input for stopping medical fluid injection executed by a stop inputter who stops the medical fluid injection, and an input executed by a setting inputter who sets or changes set value for medical fluid injection. The start inputter, the stop inputter, and the setting inputter are all healthcare practitioners such as doctors and nurses.

The input reception part 73 receives an input of identification information for identifying a start inputter who executes an input to instruct a start of medical fluid injection. Besides, the input reception part 73 receives an input of identification information for identifying a stop inputter who executes an input to instruct a stop of medical fluid injection. Further, the input reception part 73 receives an input of identification information for identifying a setting inputter who executes an input to instruct setting or changing of a set value for medical fluid injection. For instance, an input of information enabling to specify a start inputter, a stop inputter, or a setting inputter to an input screen displayed on a display 75 of the external device 7 causes the identification information to be received in the input reception part 73 and be stored in the device storage part 72.

The device communication part 74 outputs various signals for giving an instruction to the medical fluid injection device 2 based on the input received by the input reception part 73. The various signals include, for example, the start signal, the stop signal, the signal carrying start inputter information, the signal carrying stop inputter information, the setting signal, and the signal carrying setting inputter information.

The device storage part 72 stores various information. The various information includes, for example, the start instruction information, the start inputter information, the stop instruction information, the stop inputter information, the setting instruction information, and the setting inputter information.

The display 75 displays the start instruction information, the start inputter information, the stop instruction information, the stop inputter information, the setting instruction information, and the setting inputter information, and the like stored in the device storage part 72.

[Operation routine of starting medical fluid injection]

FIG. 5 is a flowchart showing a medical fluid injection method in the embodiment of the present invention. The flowchart shown in FIG. 5 shows a sequence until the start of medical fluid injection (i.e., until the start of infusion) in the medical fluid injection method in the embodiment.

As shown in FIG. 5, a healthcare practitioner such as a doctor and a nurse inputs to the external device 7 identification information for identifying the healthcare practitioner (Step S1). Specifically, the identification information is received by the input reception part 73 by inputting to an input screen displayed on the display 75 of the external device 7 as information specifying the healthcare practitioner, and then stored in the device storage part 72. An example of the identification information is an authentication ID to be inputted by a healthcare practitioner using the external device 7 when logging in the external device 7 at the start of the use thereof. Also, an input of a password may be allowed to be requested together with the input of the authentication ID.

Next, the healthcare practitioner brings the communication module 8 close to the medical fluid injection device 2 (Step S2). Specifically, in the present embodiment, the pair of engaging parts 80 of the communication module 8 is engaged with the pair of engaged parts 20 of the medical fluid injection device 2, and placed at a predetermined location of the medical fluid injection device 2 as shown in FIG. 3 and FIG. 4.

When the communication module 8 is connected to the medical fluid injection device 2, the device detection part 82 of the communication module 8 detects that the communication module 8 can communicate with the medical fluid injection device 2, and the data conversion part 83 executes transmission and reception of information between the external device 7 and the medical fluid injection device 2.

Besides, when the communication module 8 is connected to the medical fluid injection device 2, the module detection part 22 of the medical fluid injection device 2 detects that the communication module 8 can communicate with the medical fluid injection device 2 (Step S3).

Then, the main control part 31 of the medical fluid injection device 2 determines whether the medical fluid injection device 2 is in a sleep state or not (Step S4). When the medical fluid injection device 2 is in the sleep state, the power source of the medical fluid injection device 2 is in an off-state. When the medical fluid injection device 2 is not in the sleep state, the power source of the medical fluid injection device 2 is in an on-state.

When the main control part 31 determines that the medical fluid injection device 2 is in the sleep state (YES in Step S4), the main control part 31 controls the medical fluid injection device 2 to turn the power source on (Step S5), and a communication is started between the medical fluid injection device 2 and the external device 7 via the communication module 8 (Step S6). When the main control part 31 determines that the medical fluid injection device 2 is not in the sleep state (NO in Step S4), a communication is started between the medical fluid injection device 2 and the external device 7 via the communication module 8 without control of causing the power source of the medical fluid injection device 2 to be turned on (Step S6).

In the communication, the device control part 71 of the external device 7 executes an initial confirmation to the medical fluid injection device 2 to which the communication module 8 is connected. The initial confirmation includes confirmation as to which device, among a plurality of medical fluid injection devices 2 (i.e., the first medical fluid injection device 2, the second medical fluid injection device 2, and the third medical fluid injection device 2), is connected with the communication module 8. Specifically, a signal carrying identification information of a medical fluid injection device 2 is outputted from the medical fluid injection device 2, and is inputted to the external device 7 via the communication module 8. The identification information of the medical fluid injection device 2 is information assigned in advance to each medical fluid injection devices 2, for instance, as a serial number to identify each medical fluid injection device 2.

Then, the device control part 71 of the external device 7 retrieves information regarding the medical fluid injection device 2 and information regarding an additional administration device 9 from the medical fluid injection device 2 (Step S7). The information regarding the medical fluid injection device 2 includes, for instance, information regarding a set value for each medical fluid injection device 2 and the remaining battery power of the medical fluid injection device 2. The set value includes, for instance, the flow rate of medical fluid and the injection amount of medical fluid during a medical fluid injection. The information regarding the additional administration device 9 includes, for instance, the number of manipulations of the additional administration device 9, the number of effective manipulations after the lapse of lockout time, the number of ineffective manipulations during the lockout time, and the dose of additional administration. Signals carrying information regarding the medical fluid injection device 2 and information regarding the additional administration device 9 are outputted from the medical fluid injection device 2, and inputted to the external device 7 via the communication module 8, and then the information is stored in the device storage part 72.

Subsequently, the healthcare practitioner manipulating the external device 7 may change the set value for the medical fluid injection device 2 before starting a medical fluid injection by the medical fluid injection device 2. Specifically, in the present embodiment, the input reception part 73 of the external device 7 receives an input by a healthcare practitioner as to whether to change the setting for the medical fluid injection device 2 or not (Step S8). The input reception part 73 controls the display 75 of the external device 7 to perform a display of allowing the healthcare practitioner to confirm whether to change the setting for the medical fluid injection device 2 or not.

When the healthcare practitioner executes to the input screen displayed on the display 75 of the external device 7 an input to change the setting for the medical fluid injection device 2 (YES in Step S8), the device control part 71 outputs from the external device 7 a setting signal carrying the inputted setting change information. The outputted setting signal is inputted to the medical fluid injection device 2 via the communication module 8. The setting change information carried by the setting signal inputted to the medical fluid injection device 2 is stored in the storage part 32, then the setting for the medical fluid injection device 2 is changed (Step S9). On the other hand, when the healthcare practitioner executes to the input screen an input so as not to change the setting for the medical fluid injection device 2 (NO in Step S8), the set value is not changed.

The device communication part 74 of the external device 7 outputs from the external device 7 a signal carrying start inputter information for identifying the healthcare practitioner (start inputter) who executes an input to the external device 7 to instruct the start of the medical fluid injection. The outputted signal is inputted to the medical fluid injection device 2 via the communication module 8. The start inputter information carried by the signal inputted to the medical fluid injection device 2 is stored in the storage part 32 (Step S10).

Besides, when the set value is changed, the device communication part 74 of the external device 7 outputs from the external device 7 a signal carrying setting inputter information for identifying the healthcare practitioner (setting inputter) who executes an input to the external device 7 to instruct changing of the set value for the medical fluid injection. The outputted signal is inputted to the medical fluid injection device 2 via the communication module 8. The setting inputter information carried by the signal inputted to the medical fluid injection device 2 is stored in the storage part 32 (Step S10).

When the setting for the medical fluid injection device 2 is changed, the device control part 71 controls the display 75 to display the contents after the setting change to allow the healthcare practitioner to confirm the contents after the setting change (Step S11). Besides, even when the setting for the medical fluid injection device 2 is not changed, the device control part 71 controls the display 75 to display the contents of current setting to allow the healthcare practitioner to confirm the contents of the current setting (Step S11).

Then, the pump control part 34 controls the pump 51 to be primed in the medical fluid injection device 2 (Step S12). To be primed, for instance, the pump 51 is operated at a flow rate of the medical fluid temporarily set larger than the set value in an ordinary operation in order to discharge air bubbles contained in the medical fluid tube 60.

After being primed, the pump control part 34 controls the pump 51 to start medical fluid injection at a set value for the medical fluid injection device 2 (Step S13).

Finally, the healthcare practitioner brings the communication module 8 away from the medical fluid injection device 2 (Step S14). Specifically, the communication module 8 connected to the medical fluid injection device 2 is disconnected from the medical fluid injection device 2. The medical fluid injection device 2 is not configured to stop a medical fluid injection or change a set value for medical fluid injection by itself after the disconnection of the communication module 8 from the medical fluid injection device 2. This enables to prevent a person other than a certain healthcare practitioner from manipulating the medical fluid injection device 2 to stop the medical fluid injection against the will of the healthcare practitioner.

[Operation Routine of Stopping Medical Fluid Injection]

FIG. 6 is a flowchart showing the medical fluid injection method in the embodiment. The flowchart shown in FIG. 6 shows a sequence of stopping medical fluid injection in the medical fluid injection method in the embodiment.

As shown in FIG. 6, the healthcare practitioner inputs to the external device 7 identification information for identifying the healthcare practitioner (Step S21). Since the input of the identification information is similar to that in the aforementioned Step S1 shown in FIG. 5, specific description will be omitted.

Next, the healthcare practitioner brings the communication module 8 close to the medical fluid injection device 2 (Step S22). Specifically, in the present embodiment, the communication module 8 is placed at the predetermined location of the medical fluid injection device 2 as shown in FIG. 3.

When the communication module 8 is connected to the medical fluid injection device 2, the device detection part 82 of the communication module 8 detects that the communication module 8 can communicate with the medical fluid injection device 2, and the data conversion part 83 allows the external device 7 and the medical fluid injection device 2 to transmit and receive information between them.

Besides, when the communication module 8 is connected to the medical fluid injection device 2, the module detection part 22 of the medical fluid injection device 2 detects that the communication module 8 can communicate with the medical fluid injection device 2 (Step S23), and a communication is started between the medical fluid injection device 2 and the external device 7 via the communication module 8 (Step S24).

In the communication, the device control part 71 of the external device 7 executes an initial confirmation to the medical fluid injection device 2 to which the communication module 8 is connected similarly to Step S6 in FIG. 5.

Then, the device control part 71 of the external device 7 retrieves information regarding the medical fluid injection device 2 and the like from the medical fluid injection device 2 similarly to Step S7 in FIG. 5 (Step S25). A signal carrying information regarding the medical fluid injection device 2 and the like is outputted from the medical fluid injection device 2, and is inputted to the external device 7 via the communication module 8, and the information is stored in the device storage part 72.

Subsequently, the input reception part 73 of the external device 7 receives an input by the healthcare practitioner as to whether to stop the medical fluid injection operation of the medical fluid injection device 2 or not (Step S26). The input reception part 73 controls the display 75 of the external device 7 to perform a display of allowing the healthcare practitioner to confirm whether to stop the medical fluid injection operation of the medical fluid injection device 2 or not.

When the healthcare practitioner executes to the input screen displayed on the display 75 of the external device 7 an input to stop the medical fluid injection operation of the medical fluid injection device 2 (YES in Step S26), the device control part 71 outputs from the external device 7 a stop signal for stopping the medical fluid injection device 2. The outputted stop signal is inputted to the medical fluid injection device 2 via the communication module 8. When the stop signal is inputted to the medical fluid injection device 2, the main control part 31 of the medical fluid injection device 2 controls the pump 51 to stop the medical fluid injection operation of the medical fluid injection device 2 (Step S27).

The device communication part 74 of the external device 7 outputs from the external device 7 a signal carrying stop inputter information for identifying the healthcare practitioner (stop inputter) who executes an input to the external device 7 to instruct the stop of the medical fluid injection. The outputted signal is inputted to the medical fluid injection device 2 via the communication module 8. The storage part 32 stores the stop inputter information together with stop instruction information including information indicating that the instruction of stopping the medical fluid injection is given (Step S28).

Subsequently, the input reception part 73 receives an input by the healthcare practitioner as to whether to turn off the power source of the medical fluid injection device 2 or not (Step S29).

When the healthcare practitioner executes an input to turn off the power source of the medical fluid injection device 2 (YES in Step S29), the device control part 71 outputs from the external device 7 an off-signal for turning off the power source of the medical fluid injection device 2. The outputted off signal is inputted to the medical fluid injection device 2 via the communication module 8. When the off-signal is inputted to the medical fluid injection device 2, the main control part 31 controls the medical fluid injection device 2 to turn the power source off (Step S30).

Finally, the healthcare practitioner brings the communication module 8 away from the medical fluid injection device 2 (Step S31). Specifically, the communication module 8 connected to the medical fluid injection device 2 is disconnected from the medical fluid injection device 2. While the communication module 8 is disconnected from the medical fluid injection device 2, the medical fluid injection device 2 is not configured to start a medical fluid injection by itself. This enables to prevent a person other than a certain healthcare practitioner from manipulating the medical fluid injection device 2 to start the medical fluid injection against the will of the healthcare practitioner.

[Operation routine of confirming a condition of a patient]

FIG. 7 is a flowchart showing the medical fluid injection method in the embodiment of the present invention, and shows an operation routine of confirming a condition of a patient. The operation routine of confirming a condition of a patient refers to an operation of allowing a healthcare practitioner to confirm the condition of a patient by observing appearances of a patient or hearing from the patient periodically, and causing the storage part 32 of the medical fluid injection device 2 and the device storage part 72 of the external device 7 to store information regarding the confirmed condition as a history.

Since processing similar to those executed in Steps S21 to S25 shown in FIG. 6 are executed in Steps S41 to S45 shown in FIG. 7, a detailed description will be omitted.

The healthcare practitioner confirms the condition of a patient by observing appearances of the patient, or hearing from the patient, and inputs information regarding the confirmed condition to the external device 7. Specifically, the input reception part 73 of the external device 7 receives an input by a healthcare practitioner of information regarding the condition of a patient (Step S46). The input reception part 73 controls the display 75 of the external device 7 to perform a display of allowing the healthcare practitioner to input information regarding the condition of the patient.

The healthcare practitioner may input the condition of the patient, for instance, with phrases to the input screen displayed on the display 75 of the external device 7. Besides, the healthcare practitioner may select, among beforehand set options, the one adequate to the condition of the patient on the input screen. In that case, the options may include, for instance, a plurality of figures representing expressions of a patient. Specifically, the plurality of figures includes, for instance, a figure representing a smile, a figure representing a painful expression, a figure representing a normal expression being intermediate therebetween. It should be noted that the input may be executed by a patient, other than a healthcare practitioner.

When a healthcare practitioner inputs information regarding the condition of the patient to the input screen displayed on the display 75 of the external device 7 (YES in Step S46), the inputted information regarding the condition of the patient (patient information) is stored in the device storage part 72 (Step S47).

Further, the device communication part 74 of the external device 7 outputs from the external device 7 a signal carrying information regarding the condition of the patient and condition inputter information for identifying the healthcare practitioner (condition inputter) who executes an input of information regarding the condition of the patient to the external device 7. The outputted signal is inputted to the medical fluid injection device 2 via the communication module 8. The storage part 32 stores the condition inputter information together with the information regarding the condition of the patient (Step S48).

Finally, the healthcare practitioner brings the communication module 8 away from the medical fluid injection device 2 (Step S49). Specifically, the communication module 8 connected to the medical fluid injection device 2 is disconnected from the medical fluid injection device 2.

[Operation Routine of Stopping an Alarm]

FIG. 8 is a flowchart showing the medical fluid injection method in the embodiment of the present invention, and shows an operation routine of stopping an alarm.

As shown in FIG. 8, when an abnormality in the medical fluid injection device 2 is detected by the safety detector 4, the pump control part 34 of the medical fluid injection device 2 controls the pump 51 to stop the medical fluid injection, and the alarm output part 33 of the medical fluid injection device 2 controls the alarm part 53 and the alarm lamp 56 so that the alarm part 53 produces an alarm sound, and the alarm lamp 56 emits light constantly or intermittently, and the like (Step S61).

The healthcare practitioner who acknowledges an abnormality in the medical fluid injection device 2 owing to the alarm part 53 and the alarm lamp 56 takes the following measures for releasing the alarm by the alarm part 53 and the alarm lamp 56. First, the healthcare practitioner inputs to the external device 7 identification information for identifying the healthcare practitioner (Step S62). Since the input of the identification information is executed in the same manner as in the aforementioned Step S1 shown in FIG. 5, the detailed description will be omitted.

Further, since processing similar to those executed in Steps S22 to S25 shown in FIG. 6 are executed in Steps S63 to S66 shown in FIG. 8, a detailed description will be omitted.

In Step S66 shown in FIG. 8, a signal carrying information regarding the medical fluid injection device 2, such as information regarding an alarm, is outputted from the medical fluid injection device 2, and is inputted to the external device 7 via the communication module 8, and the information is stored in the device storage part 72. Then, the device control part 71 controls the display 75 so that information regarding the alarm is displayed on the display 75 of the external device 7 (Step S67).

The healthcare practitioner confirms the information regarding the alarm displayed on the display 75 of the external device 7, and gives a proper treatment depending on the contents thereof.

The input reception part 73 of the external device 7 receives an input by the healthcare practitioner as to whether to release the alarm in the medical fluid injection device 2 or not (Step S68). The input reception part 73 controls the display 75 of the external device 7 to perform a display of allowing the healthcare practitioner to confirm whether to release the alarm in the medical fluid injection device 2 or not.

When the healthcare practitioner executes to the input screen displayed on the display 75 of the external device 7 an input to release the alarm in the medical fluid injection device 2 (YES in Step S68), the device control part 71 outputs from the external device 7 a release signal for releasing the alarm in the medical fluid injection device 2. The outputted release signal is inputted to the medical fluid injection device 2 via the communication module 8. When the release signal is inputted to the medical fluid injection device 2, the alarm output part 33 of the medical fluid injection device 2 controls the alarm part 53 and the alarm lamp 56 to release the alarm in the medical fluid injection device 2 (Step S69).

The device communication part 74 of the external device 7 outputs from the external device 7 a signal carrying release inputter information for identifying the healthcare practitioner (release inputter) who executes an input to the external device 7 to instruct the release of the alarm. The outputted signal is inputted to the medical fluid injection device 2 via the communication module 8. The storage part 32 stores the release inputter information together with release instruction information including information indicating that an instruction of releasing the alarm is given (Step S70).

Subsequently, the input reception part 73 receives an input by the healthcare practitioner as to whether to resume the medical fluid injection with the medical fluid injection device 2 or not (Step S71).

When the healthcare practitioner executes an input to resume the medical fluid injection with the medical fluid injection device 2 (YES in Step S71), the device control part 71 outputs from the external device 7 a signal of resuming an operation of the medical fluid injection device 2. The outputted signal is inputted to the medical fluid injection device 2 via the communication module 8. When the signal is inputted to the medical fluid injection device 2, the pump control part 34 controls the pump 51 to resume the medical fluid injection with the medical fluid injection device 2 (Step S72).

Finally, the healthcare practitioner brings the communication module 8 away from the medical fluid injection device 2 (Step S73). Specifically, the communication module 8 connected to the medical fluid injection device 2 is disconnected from the medical fluid injection device 2.

[Modifications]

It should be noted that the present invention is not limited to the aforementioned embodiment, and for instance, the following modifications may be adopted.

In the medical fluid injection system 1 according to the aforementioned embodiment, the communication module 8 is provided. However, the communication module 8 may be omitted. In this case, various signals outputted from the external device 7 are directly received by the communication part 21 of the medical fluid injection device 2 without passing through the communication module 8.

In the aforementioned embodiment, the transmission and reception of signals between the medical fluid injection device 2 and the communication module 8 is executed via a wireless data communication by use of an infrared communication. However, the transmission and reception of signals is not limited to this communication, and may be executed via a wireless data communication other than the infrared communication, and also via a wired data communication.

In the aforementioned embodiment, the charging of the medical fluid injection device 2 is performed in a wireless charging such as an electromagnetic induction way. However, the charging is not limited to this way, and may be also performed by a wired charging.

In the aforementioned embodiment, the medical fluid injection device 2 may be configured in such a manner that when an additional administration switch 93 is manipulated by a patient, the history is stored in the storage part 32.

The pump control part 34 may be configured to control the pump 51 to start the medical fluid injection only when the communication part 21 receives the start signal. Besides, the pump control part 34 may be configured to control the pump 51 to stop the medical fluid injection only when the communication part 21 receives the stop signal.

Further, the pump control part 34 may be configured to control the pump 51 to start the medical fluid injection only when the communication part 21 receives the start signal and when the additional reception part 25 receives the start signal. In this case, the start of the medical fluid injection includes the start of the medical fluid injection of an increased dose. Besides, the pump control part 34 may be configured to control the pump 51 to stop the medical fluid injection only when the communication part 21 receives the stop signal and when the additional reception part 25 receives the stop signal. In this case, the stop of the medical fluid injection includes the stop of the medical fluid injection of an increased dose.

It should be noted that the aforementioned specific embodiments principally include the invention having the following configuration.

(1) A medical fluid injection system according to the present invention is adapted for injecting medical fluid into a patient. The medical fluid injection system includes: a plurality of medical fluid injection devices respectively corresponding to the plurality of patients; and at least one external device provided outside the plurality of medical fluid injection devices, the at least one external device being for giving an instruction of starting medical fluid injection and an instruction of stopping the medical fluid injection to the plurality of medical fluid injection devices.

Each of the medical fluid injection devices includes a pump for supplying the medical fluid, a communication part, a pump control part, and a storage part. The communication part is configured to receive: a start signal outputted from the external device to instruct a start of the medical fluid injection; a signal outputted from the external device, the signal carrying start inputter information for identifying a start inputter who executes an input to the external device to instruct the start of the medical fluid injection; a stop signal outputted from the external device to instruct a stop of the medical fluid injection; and a signal outputted from the external device, the signal carrying stop inputter information for identifying a stop inputter who executes an input to the external device to instruct the stop of the medical fluid injection. The pump control part is configured to control the pump to start the medical fluid injection when the communication part receives the start signal, and to stop the medical fluid injection when the communication part receives the stop signal. The storage part is configured to store the start inputter information together with start instruction information including information indicating that the instruction of starting the medical fluid injection is given, and the stop inputter information together with stop instruction information including information indicating that the instruction of stopping the medical fluid injection is given.

In the medical fluid injection system of the present invention, the start inputter information is stored together with the start instruction information and the stop inputter information is stored together with the stop instruction information in the storage part of each medical fluid injection device. Accordingly, it is possible to confirm who, among a plurality of healthcare practitioners, is engaged in a treatment of medical fluid injection to a patient based on the aforementioned information stored in the storage part of the medical fluid injection device corresponding to the patient after the treatment. Specific configuration will be described below.

For instance, in the medical fluid injection device disclosed in JP 2000-042102, an operation switch for starting or stopping medical fluid injection is provided in the medical fluid injection device. Accordingly, the configuration allows a plurality of concerned persons present around the medical fluid injection device, including healthcare practitioners, to easily turn on or off the operation switch provided in the medical fluid injection device. Additionally, due to a configuration of merely turning the operation switch on and off, the history as to who is engaged in the manipulation of the operation switch is not left in the medical fluid injection system. Thus, the medical fluid injection system by itself does not enable to confirm who is engaged in a treatment of medical fluid injection to a patient at a later date.

In contrast, the medical fluid injection system according to the present invention intentionally adopts a configuration which does not allow the plurality of concerned persons to start or stop the medical fluid injection by any manipulation to the medical fluid injection device itself. In the present invention, a healthcare practitioner who starts or stops medical fluid injection is required to execute an input to an external device to accomplish their intention. Based on the input, the start signal, the signal carrying the start inputter information, the stop signal, the signal carrying the stop inputter information and the like are outputted from the external device. Additionally, when the communication part of the medical fluid injection device receives the start signal or the stop signal, the medical fluid injection starts or stops, and the storage part stores the start inputter information together with the start instruction information and the stop inputter information together with the stop instruction information. Accordingly, the configuration allows to left, in the medical fluid injection device, a history as to who is engaged in the execution of an input to an external device to start or stop the medical fluid injection among the plurality of healthcare practitioners.

Owing to this, it is possible to easily prepare a nursing record for confirming at a later date the healthcare practitioner who is engaged in the treatment of medical fluid injection to each patient based on the start instruction information, the start inputter information, the stop instruction information, and the stop inputter information stored in the storage part of the medical fluid injection device corresponding to each patient. Besides, in the present invention, even if a person other than the healthcare practitioner tries to manipulate the medical fluid injection device itself, the person cannot execute the manipulation of starting or stopping the medical fluid injection. Thus, this configuration can prevent a person other than the healthcare practitioner such as a doctor and a nurse from manipulating the medical fluid injection device to start or stop the medical fluid injection against the will of the healthcare practitioner. This enables to improve the security during the medical fluid injection.

(2) The medical fluid injection system preferably further includes a communication module to which a signal outputted from the external device is inputted, wherein the communication module includes a connecting part for connecting the communication module to the medical fluid injection device; and a module communication part configured to transmit, to the medical fluid injection device to which the communication module is connected, the signal which is inputted to the communication module from the external device, the medical fluid injection device includes a display part for displaying that a state where the medical fluid injection device and the communication module connected to the medical fluid injection device are able to communicate with each other is established, and the communication part of the medical fluid injection device is configured to receive the signal which is inputted to the communication module from the external device only in communication with the communication module.

In the present configuration, when the communication module is connected to one of the plurality of medical fluid injection devices, the healthcare practitioner can confirm that a state where the connected medical fluid injection device and the communication module are able to communicate with each other is established, by watching the display part of the medical fluid injection device. Accordingly, the healthcare practitioner can confirm which, among the plurality of medical fluid injection devices, is in the operation of receiving the start signal or the stop signal outputted from the external device by watching the display part of the medical fluid injection device. Additionally, in the present configuration, the signal which is inputted to the communication module from the external device is received by the connected medical fluid injection device only by the way of communication between the communication module and the connected medical fluid injection device. Thus, this configuration can securely prevent the start signal or the stop signal outputted from the external device from being erroneously received by any untargeted medical fluid injection device.

(3) A medical fluid injection device according to the present invention is adapted for injecting medical fluid into a patient. The medical fluid injection device includes a pump for supplying the medical fluid, a communication part, a pump control part, and a storage part. The communication part is configured to receive: a start signal outputted from an external device provided outside the medical fluid injection device to instruct a start of medical fluid injection; a signal outputted from the external device, the signal carrying start inputter information for identifying a start inputter who executes an input to the external device to instruct the start of the medical fluid injection; a stop signal outputted from the external device to instruct a stop of the medical fluid injection; and a signal outputted from the external device, the signal carrying stop inputter information for identifying a stop inputter who executes an input to the external device to instruct the stop of the medical fluid injection. The pump control part is configured to control the pump to start the medical fluid injection when the communication part receives the start signal, and to stop the medical fluid injection when the communication part receives the stop signal. The storage part is configured to store the start inputter information together with start instruction information including information indicating that an instruction of starting the medical fluid injection is given, and the stop inputter information together with stop instruction information including information indicating that an instruction of stopping the medical fluid injection is given.

In the medical fluid injection device of the present invention, the start inputter information is stored together with the start instruction information in the storage part, and the stop inputter information is stored together with the stop instruction information in the storage part. Therefore, it is possible to confirm who, among a plurality of healthcare practitioners, is engaged in a treatment of medical fluid injection to a patient based on the aforementioned information stored in the storage part after the treatment. Owing to this, it is possible to easily prepare a nursing record for confirming at a later date the healthcare practitioner who is engaged in the treatment of medical fluid injection to a patient based on the start instruction information, the start inputter information, the stop instruction information, and the stop inputter information stored in the storage part of the medical fluid injection device.

Besides, in the present invention, even if a person other than the healthcare practitioner tries to manipulate the medical fluid injection device itself, the person cannot execute manipulation of starting or stopping medical fluid injection. Thus, this configuration can prevent a person other than the healthcare practitioner such as a doctor and a nurse from manipulating the medical fluid injection device to start or stop the medical fluid injection against the will of the healthcare practitioner. This enables to improve the security during the medical fluid injection.

(4) In the medical fluid injection device, the start instruction information preferably further includes information indicating a date and time when the start inputter executes the input, and the stop instruction information preferably further includes information indicating a date and time when the stop inputter executes the input.

In the present configuration, it is possible to leave, in the medical fluid injection device, a history as to when an input to the external device to start or stop medical fluid injection is executed. Thus, it is possible to chronologically confirm as to who of the healthcare practitioners is engaged in the inputting, and as to whether starting or stopping of the medical fluid injection is inputted after the treatment of medical fluid injection is given to the patient.

(5) In the medical fluid injection device, the communication part is preferably configured to further transmit to the external device the signal carrying the start instruction information, the start inputter information, the stop instruction information, and the stop inputter information.

In the present configuration, it is possible to confirm, even in the external device, a history as to who of the healthcare practitioners is engaged in the inputting of starting or stopping of medical fluid injection to the external device. In this case, there is no need to provide a display for displaying the history in the medical fluid injection device. Thus, it is possible to simplify the configuration of the medical fluid injection device.

(6) In the medical fluid injection device, the storage part is preferably configured to store information other than the information regarding the starting and the stopping of the medical fluid injection and carried by instruction signal outputted from the external device, and inputter information for identifying an inputter who executes an input to the external device to give an instruction carried by the instruction signal.

In the present configuration, information other than the information regarding the starting and the stopping of the medical fluid injection is stored in the storage part based on a signal outputted from the external device as well. Therefore, it is possible to further simplify the configuration of the medical fluid injection device. Specifically, the information other than the information regarding the starting and the stopping of the medical fluid injection includes, for example, setting instruction information including information indicating that an instruction of setting or changing the set value for medical fluid injection is given, and setting inputter information for identifying a setting inputter who executes an input of the setting instruction to the external device. Further, for instance, when the setting inputter and the start inputter are different healthcare practitioners from each other, the start inputter may confirm the contents of the setting instruction given by the setting inputter based on the setting instruction information given by the setting inputter and stored in the storage part. Thus, it is possible to double-check the contents of the setting instruction by the setting inputter and the start inputter. Besides, the information other than the information regarding the starting and the stopping of the medical fluid injection includes, for example, release instruction information including information indicating that an instruction of releasing an alarm is given, and release inputter information for identifying a release inputter who executes an input of the instruction of releasing to the external device. Further, the information other than the information regarding the starting and the stopping of the medical fluid injection includes, for example, information regarding the condition of a patient, and condition inputter information for identifying a condition inputter who executes an input of the information regarding the condition of the patient to the external device.

(7) A medical fluid injection method according to the present invention is a method for injecting medical fluid into a patient using a medical fluid injection device. The medical fluid injection method includes: a step of allowing the medical fluid injection device to receive a start signal outputted from an external device provided outside the medical fluid injection device to instruct a start of medical fluid injection; a step of starting the medical fluid injection by the medical fluid injection device when receiving the start signal; a step of storing in the medical fluid injection device start inputter information for identifying a start inputter who executes an input to the external device to instruct the start of the medical fluid injection together with start instruction information including information indicating that an instruction of starting the medical fluid injection is given; a step of allowing the medical fluid injection device to receive a stop signal outputted from the external device to instruct a stop of the medical fluid injection; a step of stopping the medical fluid injection by the medical fluid injection device when receiving the stop signal; and a step of storing, in the medical fluid injection device, stop inputter information for identifying a stop inputter who executes an input to the external device to instruct the stop of the medical fluid injection together with stop instruction information including information indicating that an instruction of stopping the medical fluid injection is given.

In the medical fluid injection method of the present invention, it is possible to confirm who, among a plurality of healthcare practitioners, is engaged in a treatment of medical fluid injection to a patient based on the aforementioned information stored in the medical fluid injection device after the treatment. Owing to this, it is possible to easily prepare a nursing record for confirming at a later date the healthcare practitioner who is engaged in the treatment of medical fluid injection to a patient based on the start instruction information, the start inputter information, the stop instruction information, and the stop inputter information stored in the medical fluid injection device corresponding to the patient. Besides, in the present invention, even if a person other than the healthcare practitioner tries to manipulate the medical fluid injection device itself, the person cannot execute the manipulation of starting or stopping the medical fluid injection. Thus, the configuration can prevent a person other than the healthcare practitioner such as a doctor and a nurse from manipulating the medical fluid injection device to start or stop the medical fluid injection against the will of the healthcare practitioner. This enables to improve the security during the medical fluid injection.

(8) In the medical fluid injection method, the start instruction information preferably further includes information indicating a date and time when the start inputter executes the input, and the stop instruction information preferably further includes information indicating a date and time when the stop inputter executes the input.

In the present method, it is possible to leave a history as to when an input to the external device to start or stop medical fluid injection is executed in the medical fluid injection device. Thus, it is possible to chronologically confirm as to who of the healthcare practitioners is engaged in the inputting, and as to whether starting or stopping of the medical fluid injection is inputted.

(9) The medical fluid injection method preferably further includes: a step of transmitting signals from the medical fluid injection device to the external device, the signals carrying the start instruction information, the start inputter information, the stop instruction information, and the stop inputter information stored in the medical fluid injection device, and storing the start instruction information, the start inputter information, the stop instruction information, and the stop inputter information in the external device; and a step of displaying on the external device the start instruction information, the start inputter information, the stop instruction information, and the stop inputter information stored in the external device.

In the present method, a healthcare practitioner can confirm at a desired time the history stored in the external device by displaying on the external device. Accordingly, there is no need to provide a display part for displaying the history in the medical fluid injection device. Thus, it is possible to simplify the configuration of the medical fluid injection device,

(10) The program according to the present invention is to be implemented in a medical fluid injection device for injecting medical fluid into a patient. The program causes the medical fluid injection device to execute: a process of allowing the medical fluid injection device to receive a start signal outputted from an external device provided outside the medical fluid injection device to instruct a start of medical fluid injection; a process of starting the medical fluid injection by the medical fluid injection device when receiving the start signal; a process of storing start inputter information together with start instruction information in the medical fluid injection device, the start inputter information being for identifying a start inputter who executes an input to the external device to instruct the start of the medical fluid injection, the start instruction information including information indicating that an instruction of starting the medical fluid injection is given; a process of allowing the medical fluid injection device to receive a stop signal outputted from the external device to instruct a stop of the medical fluid injection; a process of stopping the medical fluid injection by the medical fluid injection device when receiving the stop signal; and a process of storing stop inputter information together with stop instruction information in the medical fluid injection device the stop inputter information being for identifying a stop inputter who executes an input to the external device to instruct the stop of the medical fluid injection, the stop instruction information including information indicating that an instruction of stopping the medical fluid injection is given.

By causing the medical fluid injection device to execute the program of the present invention, it is possible to confirm who, among a plurality of healthcare practitioners, is engaged in a treatment of medical fluid injection to a patient based on the aforementioned information stored in the medical fluid injection device after the treatment. Owing to this, it is possible to easily prepare a nursing record for confirming at a later date the healthcare practitioner who is engaged in the treatment of medical fluid injection to a patient based on the start instruction information, the start inputter information, the stop instruction information, and the stop inputter information stored in the medical fluid injection device corresponding to the patient. Besides, in the present invention, even if a person other than the healthcare practitioner tries to manipulate the medical fluid injection device itself, the person cannot execute manipulation of starting or stopping medical fluid injection. Thus, this configuration can prevent a person other than the healthcare practitioner such as a doctor and a nurse from manipulating the medical fluid injection device to start or stop the medical fluid injection against the will of the healthcare practitioner. This enables to improve the security during the medical fluid injection.

The invention claimed is:

1. A medical fluid injection system for a plurality of patients, the medical fluid injection system comprising:
   a plurality of medical fluid injection devices for the plurality of patients, respectively;
   an external device for giving an instruction to start a medical fluid injection and an instruction to stop the medical fluid injection to the plurality of medical fluid injection devices, the external device being outside the plurality of medical fluid injection devices; and
   a communication module,
   wherein each of the plurality of medical fluid injection devices includes a pump for supplying the medical fluid, a communication part, a pump control part, a storage part, and a module detection part,
   wherein the communication part is configured to receive:
      a start signal outputted from the external device including the instruction to start the medical fluid injection;
      a start inputter signal outputted from the external device, the start inputter signal carrying start inputter information for identifying a start inputter who executes a start input to the external device including the instruction to start the medical fluid injection;
      a stop signal outputted from the external device including the instruction to stop the medical fluid injection; and
      a stop inputter signal outputted from the external device, the stop inputter signal carrying stop inputter information for identifying a stop inputter who executes a stop input to the external device including the instruction to stop the medical fluid injection,
   wherein the pump control part is configured to control the pump to start the medical fluid injection when the communication part receives the start signal, and stop the medical fluid injection when the communication part receives the stop signal,
   wherein the storage part is configured to store the start inputter information together with start instruction information indicating that the instruction to start the medical fluid injection is given, and the stop inputter information together with stop instruction information indicating that the instruction to stop the medical fluid injection is given,
   wherein the communication module is configured to receive the start signal or the stop signal which is outputted from the external device;
   wherein the communication module includes:

a connecting part for connecting the communication module to one of the plurality of medical fluid injection devices; and a module communication part configured to transmit, to the one of the plurality of medical fluid injection devices, the start signal or the stop signal which is inputted to the communication module from the external device, wherein the module detection part is configured to detect that the communication module is capable of communicating with the one of the plurality of medical fluid injection devices when the communication module is connected to the one of the plurality of medical fluid injection devices such that the communication module is positioned at a predetermined location of the one of the plurality of medical fluid injection devices, wherein the one of the plurality of medical fluid injection devices includes a display part for displaying that a state where the one of the plurality of medical fluid injection devices and the communication module are able to communicate with each other is established, wherein the communication part of the one of the plurality of medical fluid injection devices is configured to receive the start signal and the stop signal only by communication with the communication module, and wherein the one of the plurality of medical fluid injection devices is configured not to start the medical fluid injection, not to stop the medical fluid injection, and not to change a set value for the medical fluid injection by itself after the communication module is disconnected from the one of the plurality of medical fluid injection devices.

2. The medical fluid injection system according to claim 1, wherein:

the start instruction information further indicates a date and a time when the start inputter executes the start input; and the stop instruction information further indicates a date and a time when the stop inputter executes the stop input.

3. The medical fluid injection system according to claim 1, wherein the communication part is further configured to transmit, to the external device, transmission signals carrying the start instruction information, the start inputter information, the stop instruction information, and the stop inputter information.

4. The medical fluid injection system according to claim 1, wherein the storage part is configured to store: (i) other information than the start instruction information, the start inputter information, the stop instruction information and the stop inputter information, the other information being carried by an instruction signal outputted from the external device; and (ii) other inputter information for identifying another inputter who executes an instruction input to the external device to give another instruction carried by the instruction signal.

5. The medical fluid injection system according to claim 1, wherein the external device includes:

a display;

a device control part configured to control the display so that alarm information regarding an alarm in the one of the plurality of medical fluid injection devices is displayed on the display; and an input reception part configured to receive a release input by a healthcare practitioner as to whether to release the alarm in the one of the plurality of medical fluid injection devices or not, wherein the device control part is configured to output, from the external device, a release signal for releasing the alarm in the one of the plurality of medical fluid injection devices, when the healthcare practitioner executes the release input.

* * * * *